US012788913B2

(12) United States Patent
Fleming et al.

(10) Patent No.: US 12,788,913 B2
(45) **Date of Patent: *Nov. 10, 2026**

(54) CONTROL OF PRESSURE FOR BREATHING COMFORT

(71) Applicant: ResMed Motor Technologies Inc., Chatsworth, CA (US)

(72) Inventors: David James Fleming, Cardiff, CA (US); Michael Grunberg, Canoga Park, CA (US)

(73) Assignee: ResMed Motor Technologies Inc., Chatsworth, CA (US)

( * ) Notice: Subject to any disclaimer, the term of this patent is extended or adjusted under 35 U.S.C. 154(b) by 507 days.

This patent is subject to a terminal disclaimer.

(21) Appl. No.: 18/533,776

(22) Filed: Dec. 8, 2023

(65) Prior Publication Data

US 2024/0216626 A1 Jul. 4, 2024

Related U.S. Application Data

(63) Continuation of application No. 17/340,722, filed on Jun. 7, 2021, now Pat. No. 11,850,361, which is a
(Continued)

(51) Int. Cl.
*A61M 16/00* (2006.01)
*A61B 5/087* (2006.01)
(Continued)

(52) U.S. Cl.
CPC ......... *A61M 16/0069* (2014.02); *A61B 5/087* (2013.01); *A61B 5/097* (2013.01);
(Continued)

(58) Field of Classification Search
CPC .......... A61M 16/0069; A61M 16/0003; A61M 16/024; A61M 16/06; A61M 16/20;
(Continued)

(56) References Cited

U.S. PATENT DOCUMENTS 5,148,802 A * 9/1992 Sanders .............. A61M 16/026 128/204.23
5,740,795 A * 4/1998 Brydon ............... A61M 16/024 128/204.23
(Continued)

FOREIGN PATENT DOCUMENTS

CN 1917915 A 2/2007
DE 19540344 A1 3/1997
(Continued)

OTHER PUBLICATIONS

European Search Report for Application No. EP13790400 dated Nov. 18, 2015.
(Continued)

*Primary Examiner* — Victoria Murphy
(74) *Attorney, Agent, or Firm* — Botos Churchill IP Law LLP

(57) ABSTRACT

A respiratory treatment apparatus generates an indication of inspiration or expiration based on a measure of motor current of a flow generator. In an example, first and second current signals are derived from the measurement. The first derived current signal may be a long term measure or average of current and the second derived current signal may be a short term measure or average of current. A processor 120 determines an indication of inspiration or expiration as a function of the first and second derived current signals. The function of the first derived current signal and the second derived current signal may be a comparison of the derived current signals. The derived signals may be determined by filtering. The indication of inspiration or expiration may serve as a trigger or cycle control for changing treatment pressure in synchrony with patient respiration without measured signals from pressure, flow or speed sensors.

23 Claims, 10 Drawing Sheets

Related U.S. Application Data continuation of application No. 14/400,817, filed as application No. PCT/US2013/040749 on May 13, 2013, now Pat. No. 11,052,206.

(60) Provisional application No. 61/646,571, filed on May 14, 2012.

(51) Int. Cl.

| | |
|---|---|
| ***A61B 5/097*** | (2006.01) |
| ***A61M 16/06*** | (2006.01) |
| ***A61M 16/10*** | (2006.01) |
| ***A61M 16/20*** | (2006.01) |

(52) U.S. Cl.

CPC ...... *A61M 16/0003* (2014.02); *A61M 16/024* (2017.08); *A61M 16/06* (2013.01); *A61M 16/20* (2013.01); *A61M 2016/0021* (2013.01); *A61M 2016/0027* (2013.01); *A61M 2016/003* (2013.01); *A61M 16/0683* (2013.01); *A61M 16/1055* (2013.01); *A61M 16/107* (2014.02); *A61M 2205/3317* (2013.01); *A61M 2205/3327* (2013.01); *A61M 2205/3334* (2013.01); *A61M 2205/505* (2013.01); *A61M 2205/52* (2013.01); *A61M 2230/40* (2013.01)

(58) Field of Classification Search

CPC .......... A61M 16/0683; A61M 16/1055; A61M 16/107; A61M 2016/0021; A61M 2016/0027; A61M 2016/003; A61M 2205/3317; A61M 2205/3327; A61M 2205/3334; A61M 2205/505; A61M 2205/52; A61M 2230/40; A61B 5/087; A61B 5/097

See application file for complete search history.

(56) References Cited

U.S. PATENT DOCUMENTS

| | | | | |
|---|---|---|---|---|
| 6,237,593 | B1 | 5/2001 | Brydon | |
| 6,644,310 | B1 | 11/2003 | Delache et al. | |
| 7,100,607 | B2 | 9/2006 | Zdrojkowski et al. | |
| 7,337,778 | B2 | 3/2008 | Martin et al. | |
| 7,484,508 | B2 | 2/2009 | Younes | |
| 9,713,690 | B2 | 7/2017 | Somaiya et al. | |
| 2007/0017518 | A1 | 1/2007 | Farrugia et al. | |
| 2009/0050155 | A1 | 2/2009 | Alder et al. | |
| 2011/0155134 | A1* | 6/2011 | Farrugia ........... | A61M 16/0069 128/204.23 |

FOREIGN PATENT DOCUMENTS

| | | | |
|---|---|---|---|
| JP | 6155985 | A1 | 12/2000 |
| JP | 2001513387 | A | 9/2001 |
| JP | 2005007187 | A | 1/2005 |
| JP | 2007144098 | A | 6/2007 |
| JP | 2007521889 | A | 8/2007 |
| WO | 2005077447 | A1 | 8/2005 |

OTHER PUBLICATIONS

International Search Report for Application No. PCT/US2013/040749 dated Oct. 4, 2013.

* cited by examiner

CONTROL OF PRESSURE FOR BREATHING COMFORT

CROSS REFERENCE TO RELATED APPLICATIONS

This application is a continuation of U.S. patent application Ser. No. 17/340,722, filed Jun. 7, 2021, which is a continuation of U.S. patent application Ser. No. 14/400,817, filed Nov. 13, 2014, which is a national phase entry under 35 U.S.C. § 371 of International Application No. PCT/US2013/040749, filed May 13, 2013, published in English, which claims priority from U.S. Provisional Patent Application No. 61/646,571, filed May 14, 2012, the disclosures of all of which are incorporated herein by reference.

FIELD OF THE TECHNOLOGY

The present technology relates to methods and apparatus for detecting indicators of respiratory flow during assisted respiration including ventilation, Positive Airway Pressure (CPAP) treatment or Non-Invasive Positive Pressure Ventilation (NIPPV). More particularly, the technology relates to controlling a pressure treatment supplied to a patient during assisted respiration to provide improved comfort for breathing. The method and apparatus may be used to treat Sleep Disordered Breathing (SDB), snoring disorders, or other respiratory disorders.

BACKGROUND OF THE TECHNOLOGY

CPAP treatment of SDB may involve the delivery of a pressurised breathable gas, usually air, to a patient's airways using a conduit and mask. Gas pressures employed for CPAP typically range from 4 cm H2O to 28 cm H2O, at flow rates of up to 180 L/min (measured at the mask), depending on patient requirements. The pressurised gas is said to act as a pneumatic splint for the patient's airway, preventing airway collapse, especially during the inspiratory phase of respiration. In a Bi-Level PAP device, a higher pressure is provided during an inspiration phase of the breathing cycle and a lower pressure is provided during an expiration phase of the breathing cycle in order to provide improved breathing comfort for the patient. In some CPAP devices, an expiratory pressure relief, which may be considered a drop in pressure of generally 1-3 cm $H_2O$ from an inspiratory pressure treatment setting, is provided during an expiration phase compared to the inspiration phase.

CPAP apparatus typically include a flow generator or blower for supplying pressurised respiratory gas, such as air, to the patient via an air delivery tube leading to a patient interface, such as a nasal or oronasal mask, or nasal cushion or nasal pillows arrangement.

BRIEF SUMMARY OF THE TECHNOLOGY

One form of the present technology involves an improved method and apparatus adapted to control the pressure supplied to a user by a positive airway pressure (PAP) device based on motor current measurements. Such an apparatus may be implemented without including flow or pressure sensors to measure the airflow.

Another form of the present technology includes a method and apparatus adapted to determine the changes in respiratory flow based on a measure of current supplied to a blower in a positive airway pressure (PAP) device. The detected changes in respiratory flow may be used to control the speed of the blower and consequently the pressure supplied by the blower.

Another form of the technology relates to a method and apparatus adapted to detect transitions between inspiration to expiration by assessing changes in the current supplied to a motor of a PAP device.

Another form of the technology relates to a method and apparatus adapted to detect transitions between inspiration to expiration by assessing changes in the current supplied to a motor of a PAP device and controlling the motor to deliver a first pressure during inspiration and a second pressure during expiration.

Some embodiments of the technology involve a method of a respiratory treatment apparatus for determining an indication of inspiration or expiration. The method may include measuring current supplied to a blower configured to provide a respiratory treatment. The method may also include deriving first and second current signals from the measured current. The first derived current signal may be a long term measure of current and the second derived current signal may be a short term measure of current. The method may also include determining with a processor an indication of inspiration or expiration as a function of the first derived current signal and the second derived current signal.

In some cases, the first derived current signal may be derived by filtering of the measured current. Also, the first derived current signal may be derived by a low pass filter with a first time constant. Optionally, the second derived current signal may be derived by filtering of the measured current. Moreover, the second derived current signal may be derived by a low pass filter with a second time constant. In some cases, the first time constant may be on the order of a time period shorter than an average breath and the second time constant may be on the order of a time period greater than an average breath.

Optionally, the function of the first derived current signal and the second derived current signal may include a comparison of the first derived current signal and the second derived current signal. In some cases, the method may also include adding a compensation signal to the first derived current signal. In some cases, the method may further include adding a compensation signal to the first derived current signal based on the indication of inspiration or expiration. Similarly, different compensation signals may be added to the first derived current signal based on the indication of inspiration or expiration. In some embodiments, the function of the first derived current signal and the second derived current signal may involve a comparison of the second derived current signal and the sum of the first derived current signal and a compensation signal. The method may also include maintaining the second derived current signal with blanking values rather than the measure of current during a transition of the indicator of inspiration or expiration. The method may further include controlling with the processor setting of a pressure treatment generated by the blower based on the indication of inspiration or expiration.

Some embodiments of the present technology may include a respiratory treatment apparatus for determining an indication of inspiration or expiration. The apparatus may include a blower, having an impeller and motor. The blower may be configured to generate a pressure treatment to a patient interface. The apparatus may also include a current sensing circuit configured to generate a current signal representative of current supplied to the motor. The apparatus may also include a processor coupled to the sensing circuit.

The processor may be configured to (a) derive first and second current signals from the current sensing circuit where the first derived current signal may be a long term measure of current and the second derived current signal may be a short term measure of current, and (b) determine an indication of inspiration or expiration as a function of the first derived current signal and the second derived current signal.

In some cases, the processor may include a filter to generate the first derived current signal by filtering of the measured current. The filter may include a low pass filter with a first time constant. Optionally, the apparatus may further include a further filter to generate the second derived current signal by filtering of the first derived current signal. In some cases, the processor may further include a further filter to generate the first derived current signal by filtering of the second derived current signal where the further filter includes a low pass filter with a second time constant, wherein the first time constant may be on the order of a time period shorter than an average breath and the second time constant may be on the order of a time period greater than an average breath.

Optionally, the function of the first derived current signal and the second derived current signal may include a comparison of the first derived current signal and the second derived current signal. Moreover, the processor may be further configured to add a compensation signal to the first derived current signal. The processor may also be further configured to add a compensation signal to the first derived current signal as a function of the determined indication of inspiration or expiration. In some cases, the processor may be configured to add different compensation signals to the first derived current signal based on the determined indication of inspiration or expiration. In some cases, the function of the first derived current signal and the second derived current signal may include a comparison of the second derived current signal and the sum of the first derived current signal and a compensation signal. Still further, processor may also be configured to maintain the first derived current signal with blanking values rather than the measure of current during a transition associated with the determined indicator of inspiration or expiration. Also, the processor may be further configured to control setting of a pressure treatment generated by the blower based on the indication of inspiration or expiration. Of course, portions of the aspects may form sub-aspects of the present invention. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The above and other features and advantages of the present technology are further described in the detailed description which follows, with reference to the drawings, and by way of non-limiting exemplary embodiments of the present technology wherein.

Figure 7A:
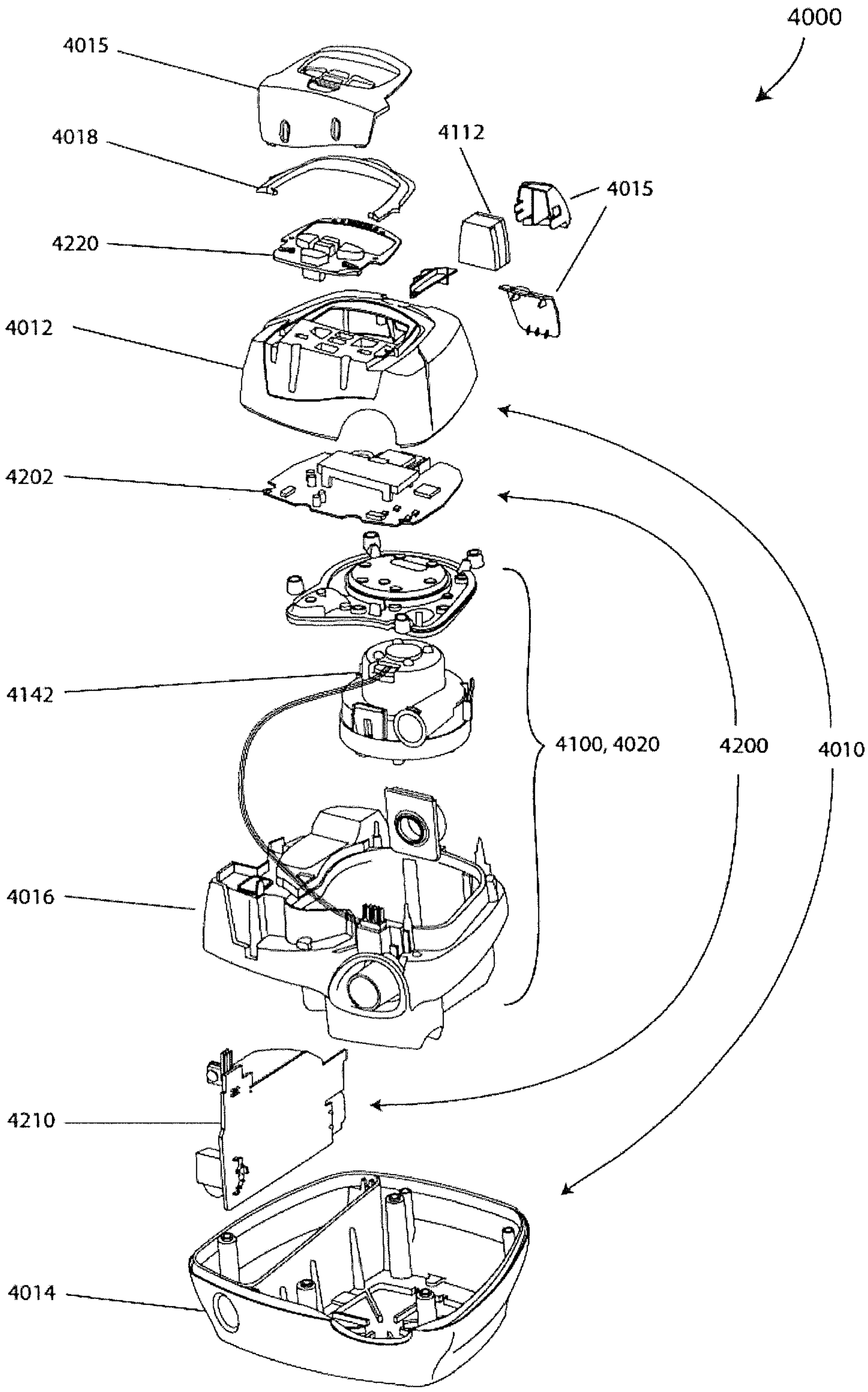
Figure 8:
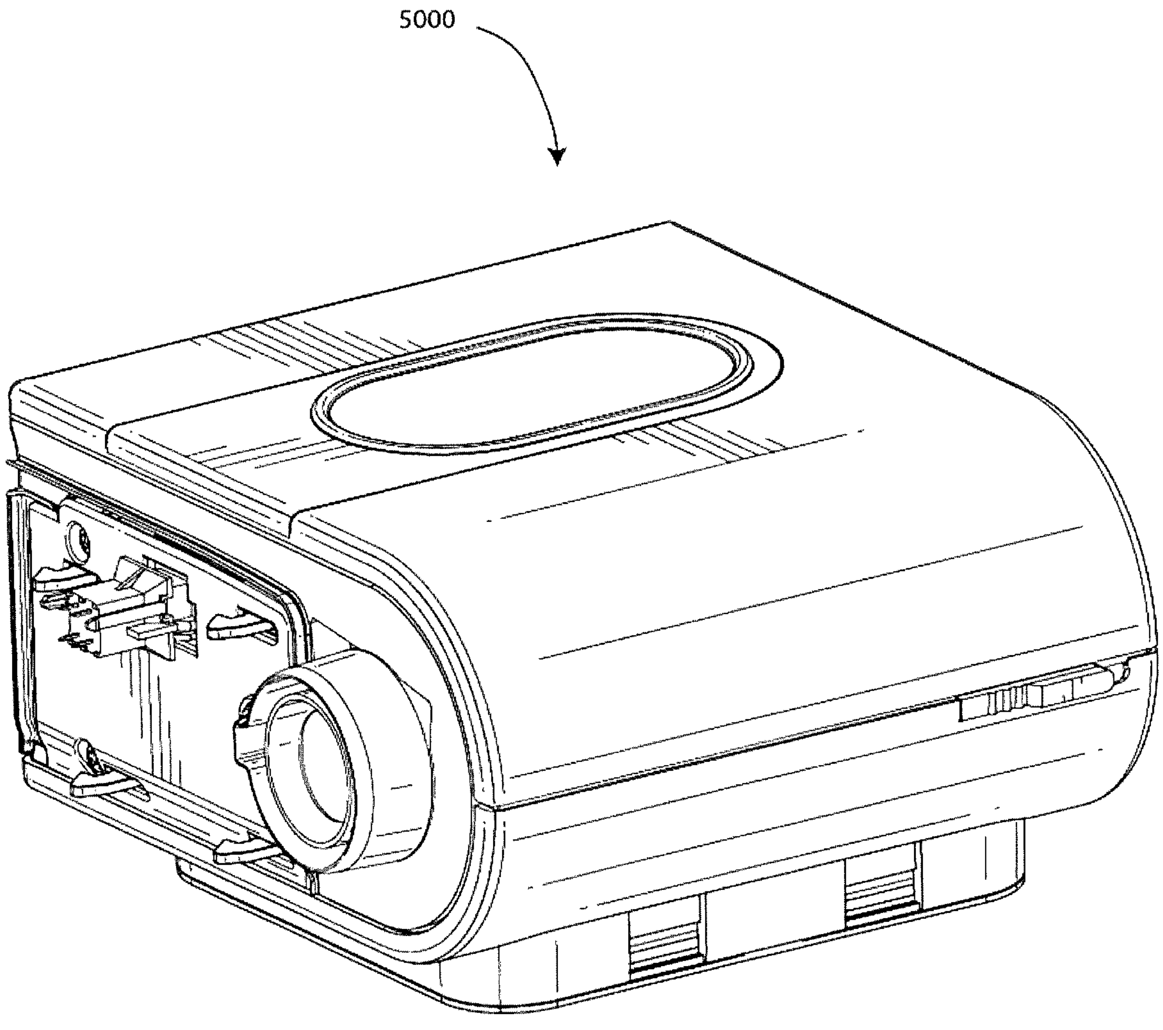

FIG. **7*a*** shows a PAP device in accordance with one form of the present technology;

FIG. **7*b* shows a schematic diagram of the pneumatic circuit of a PAP device of FIG. 7*a***. The directions of upstream and downstream are indicated;

FIG. **7*c* shows a schematic diagram of the electrical components of the PAP device of FIG. 7*a*; and FIG. 8** shows a humidifier in accordance with one aspect of the present technology.

DETAILED DESCRIPTION OF THE TECHNOLOGY

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise," "comprised" and "comprises" where they appear.

The term "air" will be taken to include breathable gases, for example air with supplemental oxygen. It is also acknowledged that blowers or flow generators described herein may be designed to pump fluids other than air.

A PAP device 110 may include a flow generator or blower 112 having a motor 114 configured to drive an impeller 118 coupled to a rotor 116 of the motor 114 to generate a supply of pressurized gas or air. The motor 114 is controlled by a processor 120 that provides a drive signal to the motor 114 to control the speed at which the rotor 116 and consequently the impeller 118 rotates within a volute or other flow inducing chamber. In a preferred embodiment, the motor 114 may be a sensorless motor (e.g., no commutation or position sensor) such as one without a Hall Effect sensor where the speed of the motor may be determined by measuring the back electromotive force (EMF) of the motor as the rotor 116 rotates. The processor 120 comprises a feedback control loop to maintain the motor 114 at the desired motor speed by comparing the measured speed of the blower to the desired speed of the blower and adjusting the motor voltage or current to maintain the desired speed. In some cases, the technology may be implemented without additional sensors (e.g., no flow sensor and/or no pressure sensor).

The characteristics of the systems and blower have preferably been predetermined, for example pressure drop along the air delivery conduit, etc. Thus, the relationship between motor speed and pressure delivered is known. Consequently, the PAP device controls the speed of the blower to provide the desired pressure. In some cases, there may not be an actual pressure measurement determined by a pressure sensor. Although, in some cases, pressure may be estimated or calculated from known or measured parameters. In some cases, the current signal analysis described herein may permit the PAP device or other respiratory pressure treatment device to operate with a minimal sensing configuration (e.g., only current sense resistor(s)) so as to permit implementation without a flow sensor, pressure sensor and/or speed sensor. However, as illustrated in more detail herein, in some cases one or more of such sensors may be implemented with the apparatus. In such cases, the current signal analysis may serve as a redundant cycling or triggering process to check operations based on the sensors or may otherwise be activated as a back-up process in the event of a detected fault in one or more of the sensors.

The PAP device 110 may optionally include a user interface 122 and/or controls 124 such as one of more buttons and/or dials to allow the user to interact with the device, for example an on/off button.

The PAP device typically includes a gas outlet 126 coupled to an air delivery conduit (not shown) to deliver a flow of the pressurized gas generated by the blower 112 to a patient interface unit (not shown) such as a mask or nasal assembly.

In certain examples, the PAP device may be configured to deliver a first pressure during an inspiration phase of the breathing cycle and a second pressure during the expiration phase of the breathing cycle. The first pressure is higher than or equal to the second pressure. The difference in pressure between the first pressure and the second pressure is called the pressure support and such a pressure difference may be set to 0, 1, 2 or 3 cm $H_2O$ to provide an expiratory pressure relief (EPR). Higher pressure support values may be provided when the PAP device is a BiLevel PAP device. Preferably the first pressure is between 4 cm $H_2O$ and 28 cm $H_2O$, and the second pressure is between 2 cm $H_2O$ and 20 cm $H_2O$.

During respiration, the flow delivered to the patient interface will vary with the user's respiratory cycle. Such changes in flow will result in changes in the level of current provided to maintain the blower at the desired motor speed to deliver the appropriate pressure. These changes in the level of current may be used to assess the changes in flow occurring and detect the transitions from inspiration to expiration and vice versa from expiration to inspiration. Thus, in some embodiments, the current supplied to the bridge drive circuit of the motor of the blower, rather than the phase current of the motor, may be used as a proxy for flow.

In some such cases, the current may serve as the proxy for flow at certain times. For example, when the voltage applied to the motor (via a bridge circuit) is likely to be approximately constant. In the case of an implementation of pulse width modulation (PWM) of a source voltage (e.g., a bus voltage) to control the motor, a lower voltage to the motor than the bus voltage will be applied to the motor (e.g., the applied voltage may be equal to the bus voltage times a PWM percentage).

Alternatively, in some embodiments, the power to the blower may be used as the proxy for flow. In such a case, the current signal of the supplied current to the blower may be provided to a multiplier circuit with a signal representing the voltage to the motor. Such a power signal may then be applied to the processes described herein rather than the current signal.

Thus, in some embodiments, a motor current signal may be measured and may be recorded. The measured motor current signal MCS, which may optionally be sampled data representing the signal, may then be processed by a processor or processing circuit, such as an analog processing circuit (e.g., an analog processor) or a digital processing circuit (e.g., a digital processor) or any combination thereof.

Figure 1:
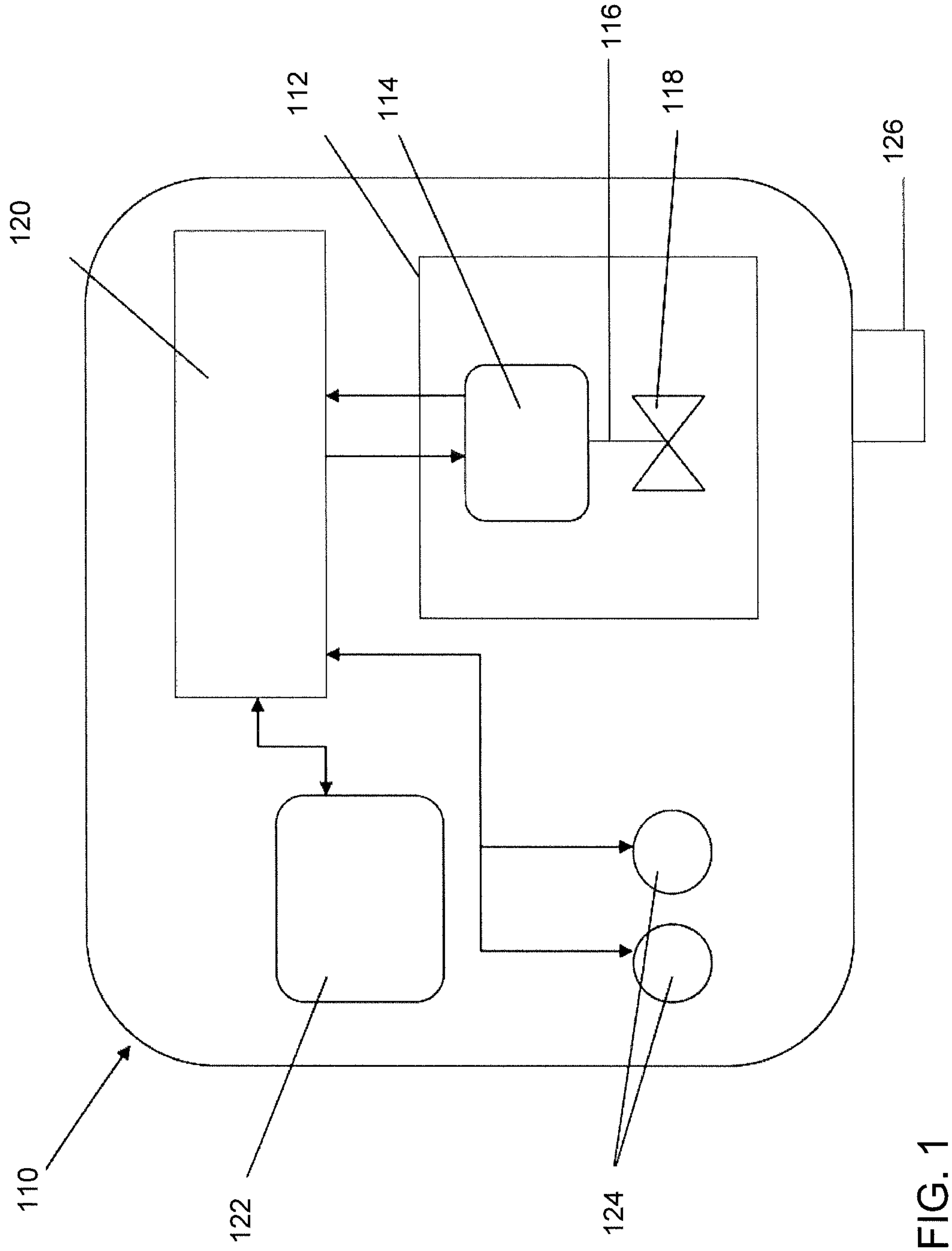
FIG. 1 shows a schematic diagram illustrating a flow detection system according to an aspect of the technology.
Figure 2:
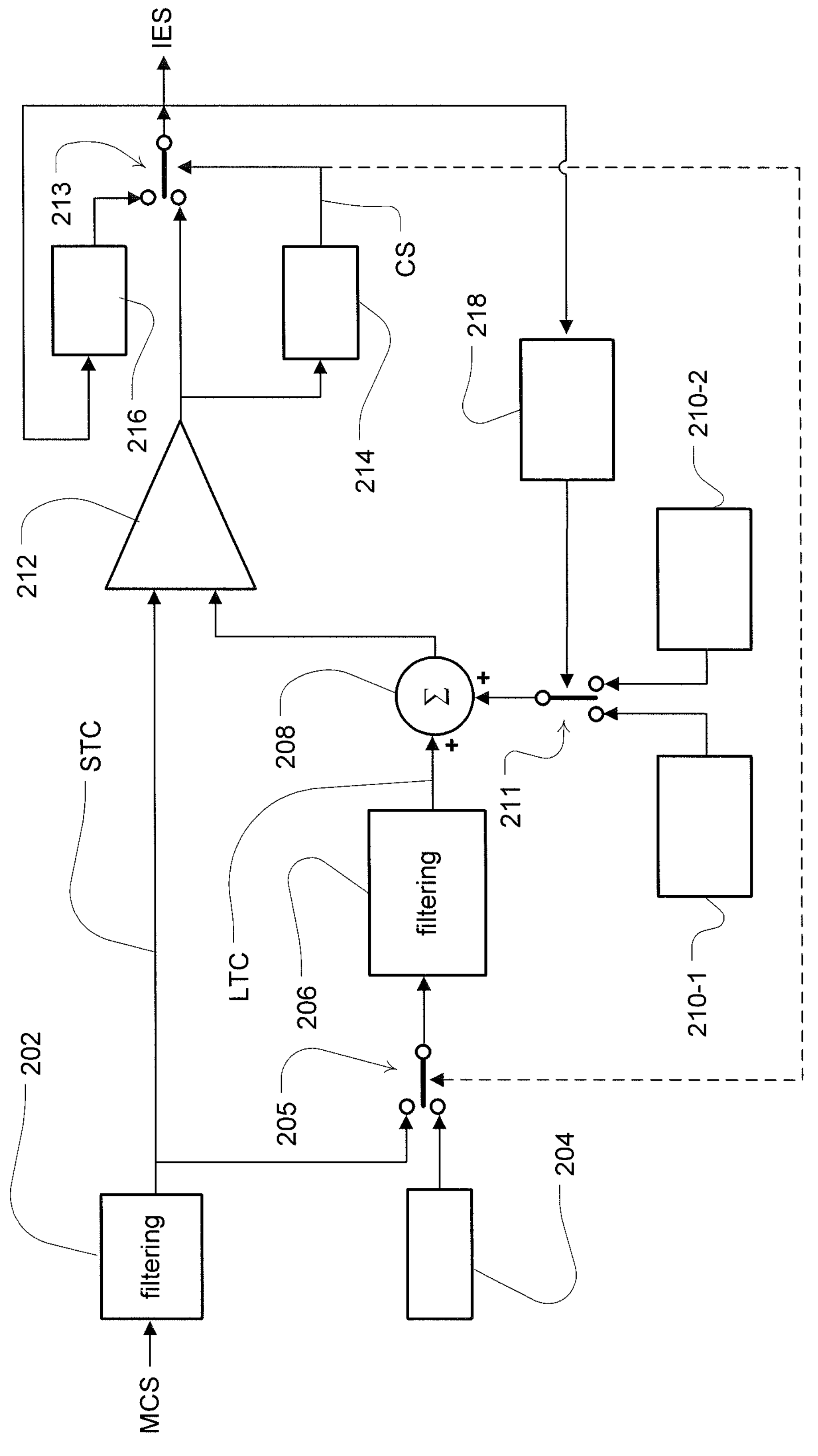
FIG. 2 is an illustration of example elements of a processor that may be implemented for the current analysis in some embodiments of the present technology.

Example elements of an embodiment of such a processor or processing circuit are illustrated in FIG. 2. In some cases, the motor current signal MCS that is applied to the processing circuit may be measured using one or more current sensing resistors. Optionally, other devices may be implemented to measure the current such as Hall sensors, current transformers, printed circuit board (PCB) traces (a variation of the resistor), etc. The current may be measured in the motor leads or a common bridge bottom. The current may also be measured in the bridge top or bottom such as with two or three sensors. In some cases, the measured current may be an average of the phase current of the coils of the motor.

The measured motor current signal MCS may then be processed, such as by filtering as shown in FIG. 2, such as with one or more filters to derive various assessment signals. For example, the measured motor current signal MCS may be filtered with a filter 202, such as a low pass filter (e.g., a first order low pass filter with a 53 HZ or 160 Hz cut off frequency, a moving average filter, a higher order filter, or similar), to remove noise or disturbances in the signal. The signal derived from such filtering may be considered an instantaneous or short term motor current signal STC or a short term average measure of current. Such a signal may be taken as an indicator of the present level of flow, without a flow sensor. Based on the chosen parameters or time constant(s) of such filtering, the short term measure of current may be considered a measure of motor current over a time period of less than one average breath, for example less than half an average breath.

A long term motor current signal LTC may also be derived by filtering, such as with a further filter 206 illustrated in FIG. 2. For example, the short term motor current signal STC may be filtered with a filter 206, such as a low pass filter (e.g., a first order low pass filter with a 0.003 HZ cut off frequency, a moving average filter, a higher order filter or similar). The signal derived by such processing may be taken as an indication of a base level of flow due to leak etc. The leak may include deliberate leak from the patient interface and/or other leak due to fitting issues with the system. As such, and based on the parameters or time constant(s) of the filtering, the long term motor current LTC, may be considered a measure of current over a predetermined time period that is longer than a single breath. As such, it may also be considered a long term average measure of current. For example, it may be derived over a duration of multiple breaths, such as in a range of 2-10 breaths, such as 4, 5, 6, 7 or 8 breaths. Alternatively, the predetermined time period may include the time taken to record a predetermined number of the previous current values or may be set as a time based limit, such as the current values recorded over the preceding predefined number of seconds, e.g., over the preceding 10 to 90 seconds, 15 to 50 seconds, 20 to 40 seconds, such as 30 seconds or longer. Although it is to be understood that other time periods for the long term motor current may be utilised.

In the case of digital processing, the motor current or the derived signals from the filtering thereof, may be sampled at a sampling rate of 1-20 KHz, such as 5 kHz. Thus, in some cases the long and short term derived measures may be calculated with sampled data accordingly. However, those skilled in the art would understand that other sampling rates may be implemented.

Optionally, in some embodiments of the technology, during known speed changes by the motor, such as during changes in speed to alter the pressure between an inspiration phase and an expiration phase, the calculation of the filtering may be adjusted to avoid applying current into the filters that is associated with such changes. For example, the filtering to derive the long term motor current signal may be paused or temporarily stopped based on such changes. Alternatively, current values obtained during such changes may be excluded from the calculation of the long term measure.

Still further, in some versions, maintenance values or "blanking values", which may be numerical constants that are calculated so as to add no net value to the content of the filter (e.g., the long term average of the filter), may be optionally applied to the filtering, rather than values of, or based, on actual motor current, in order to maintain the state of the filter during deliberate/known changes in motor speed. For example, a motor acceleration/deceleration maintenance factor may be applied to the filter 206 during such known speed changes by the motor. An example of such processing may be considered in reference to FIG. 2. A switching or decision element 205 may selectively apply either the short term motor current STC to the filter 206 or the maintenance signal from a maintenance signal generator 204 or other buffer. The condition or logic for such a switching element is discussed in more detail herein.

To determine changes in flow such as for detecting the different phases of breathing, the instantaneous or short term motor current STC may be compared with the long term motor current LTC. Such a comparison may serve to provide an indication of changes in respiratory flow, such as an inspiration or expiration indicator or signal IES. An example of such processing may be considered with reference to the comparator element 212 of FIG. 2. For example, when the instantaneous or short term motor current is greater than the long term motor current, the comparison may be taken as an indication that the flow is increasing. When the instantaneous or short term motor current is less than the long term motor current, the comparison may be taken as an indication that the flow is decreasing. Such an increasing flow may serve as an indication that inspiration is occurring and such a decreasing flow may serve as an indication that expiration is occurring. Thus, the commencement of the different phases of the breathing cycle of a patient, inspiration and expiration, may be determined by monitoring the changes in flow based on this evaluation of changes in the instantaneous or short term current compared to the long term current. The detection of the commencement of the different phases of breathing can be used to provide trigger and/or cycling signals, such as for a motor control processor that alters the motor speed for changing the delivered pressure as required for the different breathing phases. For example, based on the comparison, the comparator 212 may be configured to generate a positive or high signal in the event of expiration and a null or low signal in the event of inspiration (or vice versa). The positive IES signal may then serve as a control signal to set a speed change of the blower for an expiratory pressure. The null or low IES signal may then serve as a control signal to set another speed change of the blower for an inspiratory pressure.

In some embodiments, a compensation factor may optionally be implemented to compensate for delays or lags between determining a phase change in the patient's respiratory cycle from the current and adjusting the motor speed for changing the delivered pressure. The implementation of the compensation factor can thereby cause the IES signal to adjust the motor speed (and the resulting pressure) slightly earlier such that the actual change in motor speed is more likely to be in synchrony with changes in the patient or user's respiratory breathing cycle. Such an embodiment may be considered with reference to FIG. 2, which shows compensation generator 210-1, 210-2 and a combiner element, such as adder 208. In this example, the adder 208 selectively adds a compensation signal from a generator or buffer based on the state of the IES signal. A switching or decision element 211 may selectively apply the different compensation signals to the adder 208 from multiple signal generators 210-1, 210-2 (such as one or more signal buffers). The condition or logic for such a switching element is discussed in more detail herein with reference to switching control element 218. Essentially, the switching control element 218, based on the IES signal (or the state of detected inspiration or expiration) may control the switching or decision element 211 to apply either a positive or negative compensation factor to the long term motor current signal at the times discussed herein in reference to the state machine of FIG. 3.

In the system that employs compensation factors, the instantaneous or short term motor current is compared to an adjusted long term motor current that represents the long term motor current plus or minus a compensation factor. In such a case, if the instantaneous or short term motor current is less than the long term motor current minus the compensation factor, the comparator 212 will generate an IES signal indicative of expiration such that the motor may, in response thereto, be adjusted to the expiration pressure motor speed. Similarly, if the instantaneous or short term motor current is greater than the long term motor current plus the compensation factor, the comparator 212 will generate an IES signal indicative of inspiration such that the motor speed may, in response thereto, be adjusted to the inspiration pressure motor speed.

In some embodiments, the compensation factor (CF) may be a set buffer level of current, for example 2-10 mA. In alternative arrangements, the compensation factor may be automatically determined as a proportion, such as a fraction or percentage, of the long term motor current. In a further arrangement the compensation factor may be calculated as a function of a detected peak in current during the inspiration and/or expiration phase. In such an arrangement the peak current during the inspiration and/or expiration phase is detected and the compensation factor is determined as a proportion (e.g., a fraction or percentage) of the peak value. In alternative arrangements, the compensation factor may be determined based on the time since the last IES transition.

As further illustrated in FIG. 2, the IES signal output of the comparator 212 may optionally be applied to a switching or decision element 213, a buffer 216 and an edge activated blanking timer 214. A recent state of the IES signal may be held in the buffer 216 and output from the buffer to the switching or decision element 213. Thus, the switching or decision element 213 will selectively output either the current state of the IES signal from the comparator or a prior but recent state of the IES signal from the buffer 216. In this regard, the edge activated blanking timer 214 will generate a control signal CS for the switching or decision element 213. The process of the edge activated blanking timer 214 will include an edge detector to detect changes in the IES signal output from the comparator. The detection of the edge may then start a timer with a predetermined time interval. During the predetermined time interval, the edge activated blanking timer 214 will output a control signal to set the switching or decision element 213 to select the previous, recent state of the IES signal held in the buffer 216 rather than the IES signal from the comparator. At other times, the edge activated blanking timer 214 will output a control signal CS to set the switching or decision element 213 to select the IES signal from the comparator rather than the prior but recent state of the IES signal held in the buffer 216. Such control may permit a more stable IES signal during a time of change in the speed of the motor such as when the motor is changing between an inspiratory speed setting for an inspiratory pressure and an expiratory speed setting for an expiratory pressure. Accordingly, the predetermined time of the timing interval of the edge activated blanking timer 214 may be chosen so as to use the output of the buffer 216 as the IES signal for an amount of time to equal or exceed a typical time associated with the aforementioned changes in motor speed.

Additionally, as previously described with reference to the maintenance signal generator 204, the control signal CS output by the edge activated blanking timer 214 may be applied to control the switching or decision element 205. In this regard, the input to the filter 206 may be selectively changed to an output of the maintenance signal generator 204. Thus, the edge activated blanking timer 214 may selectively control the application of the maintenance signals to the filter during the predetermined time of the timing interval of the edge activated blanking timer 214. Thus, the filter 206 may receive output of the maintenance signals for an amount of time to equal or exceed a typical time associated with the changes in motor speed, such as the changes associated with the inspiratory speed setting and/or the expiratory speed setting. At other times, the switching or decision element 205, under control of the edge activated blanking timer 214, may permit short term current to be applied to the filter 206.

Figure 3:
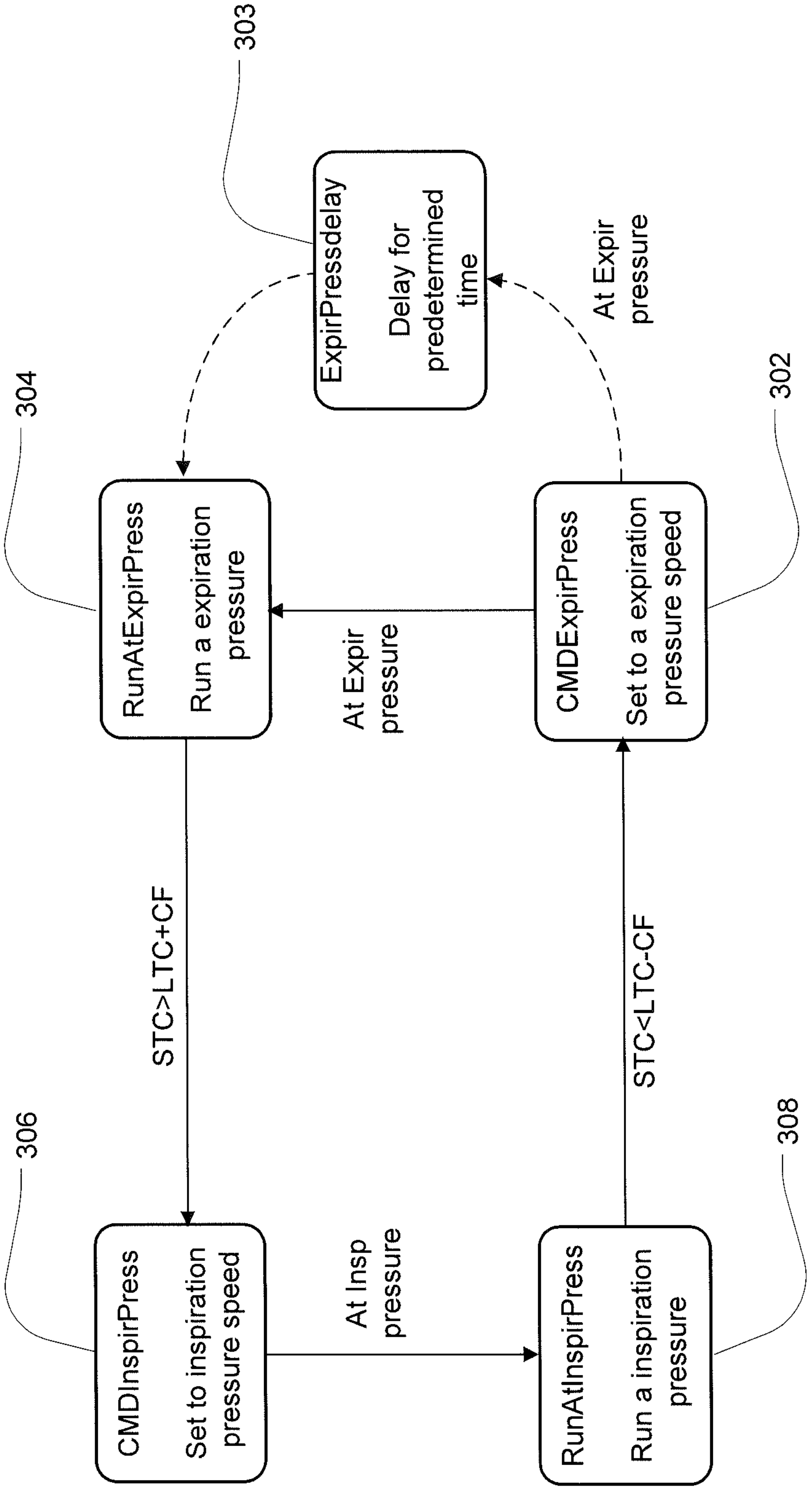
FIG. 3 is a state machine diagram for a blower speed controller for generating the pressure supplied by a blower according to an aspect of the technology.

FIG. 3 is a schematic of an exemplary state machine for the motor speed controller to control the motor speed and consequently the pressure delivered by the blower. In state 1, 302, the motor is provided with a command signal to set the motor speed at the expiration motor speed. As noted above, the recording of the current values during this speed transition phase may be paused or temporarily stopped or a deceleration maintenance factor may be applied for filtering processes to compensate for the changes in current resulting from the deceleration. Once the expiration motor speed is reached (which may be determined based on a comparison of the desired speed with a measured or estimated speed, or a lapse of a predetermined time period), the motor speed controller moves to State 2, 304, wherein the motor is signalled to continue running to maintain the expiration pressure until such time as the short term motor current (STC) is greater than the long term motor current (LTC) plus a compensation factor (CF). When the short term current (STC) is greater than the long term current (LTC) plus a compensation factor (CF), the motor speed controller transitions to state 3, 306, and a command signal is sent to the motor to increase the motor speed to the inspiration motor speed. Again as noted above, during this state, the recording of the current values during this speed transition phase may be paused or temporarily stopped or an acceleration maintenance factor utilised for the filter processing to compensate for the changes in current resulting from the acceleration. When the set inspiration motor speed is reached (which may be determined based on a comparison of a desired speed and a measured or estimated speed, or a lapse of a predetermined time period), the motor speed controller transitions to state 4, 308. During state 4, 308, the motor is signalled to continue running to maintain the inspiration pressure motor speed until such time as the short term current (STC) is less than the long term current (LTC) minus a compensation factor (CF). When the short term current (STC) is less than the long term current (LTC) minus a compensation factor (CF), the motor speed controller transitions back to state 1, 302 and the cycle continues.

In certain optional arrangements the motor controller may include a further state 1.5, 303, between state 1, 302, and state 2, 304. In state 1.5, 303, a predetermined expiration pressure delay is set before the short term current (STC) is compared to the long term current (LTC). Such as delay may ensure that expiration occurs for a minimum time period and/or ensure that false triggers into state 3, 306, from state 2, 304, are avoided. In a further arrangement (not shown) a similar inspiration pressure delay state 3.5 may be added between state 306 and state 308 to ensure that inspiration is allowed to occur for a minimum time period.

In certain examples, the motor may be allowed to freewheel such that no active braking occurs for the change in motor speed that changes the delivered pressure from the inspiration motor speed to the expiration motor speed. The freewheeling to slow down the motor may use the method or apparatus as described in U.S. Patent Application Publication No. 2007/0017518, the disclosure of which is incorporated herein in its entirety. Alternatively, some form of braking of the motor may be utilised to control the transition between inspiration and expiration.

In certain systems when therapy first commences, there may be a delay in calculating the long term motor current until a second predetermined time period has passed. In certain examples the second predetermined time period may be at least as long as the predetermined time period used in calculating the long term average current. The delay may provide a settling time for the user to adjust to the commencement of therapy and the device to begin recording current values. The device may be configured to provide a single constant pressure (i.e., a single set motor speed) during both inspiration and expiration during this settling time.

Alternatively the long term motor current may be initially set at an initial predetermined average current value. The initial predetermined average current value may be preset in the device due to pre-characterisation of the system during manufacture or be set based on the long term average current from a previous therapy session. In addition or alternatively in certain example devices the predetermined time period may initially be shortened, (e.g., to 10, 15 or 20 seconds), at the commencement of therapy, (e.g., for the first 1-2 minutes of therapy), to provide a faster calculation of the average long term current. In such devices the current values may be recorded upon commencement of therapy to assess the changes in flow to detect the different breathing phases with or without making adjustments to the pressure during the different breathing phases.

Although not shown in FIG. 2, in some embodiments, an additional "observer" process component may be included. The observer, based on system parameters known at design time (such as motor torque constant, system inertia, etc.) may be configured to estimate the portion of the current supplied to the motor that is due to acceleration/deceleration of the motor during pressure changes. With this estimate, the current may be adjusted before the filtering described herein. As such, the short term motor current that is indicative of the patient flow (after subtracting the long term motor current) may be taken as a more continuous indicator of the state of the patient's respiratory flow, rather than a more simple indication of cither inspiration or expiration. Such a signal may then serve as a basis for controlling changes to treatment pressure in a more continuous fashion within a patient's respiratory cycle, as opposed to a simple dual level control indicator.

By way of further example, although the processing circuit has been illustrated as circuit elements in FIG. 2, it will be understood that the processes of these elements may be implemented with the algorithms or processing of a digital processor. In such a case, the digital processor may include integrated chips, a memory and/or other control instruction, data or information storage medium. For example, programmed instructions encompassing the process methodologies may be coded on integrated chips in a memory or otherwise form an application specific integrated chip (ASIC). Such instructions may also or alternatively be loaded as software or firmware using an appropriate data storage medium.

Example System Architecture

Figure 4:
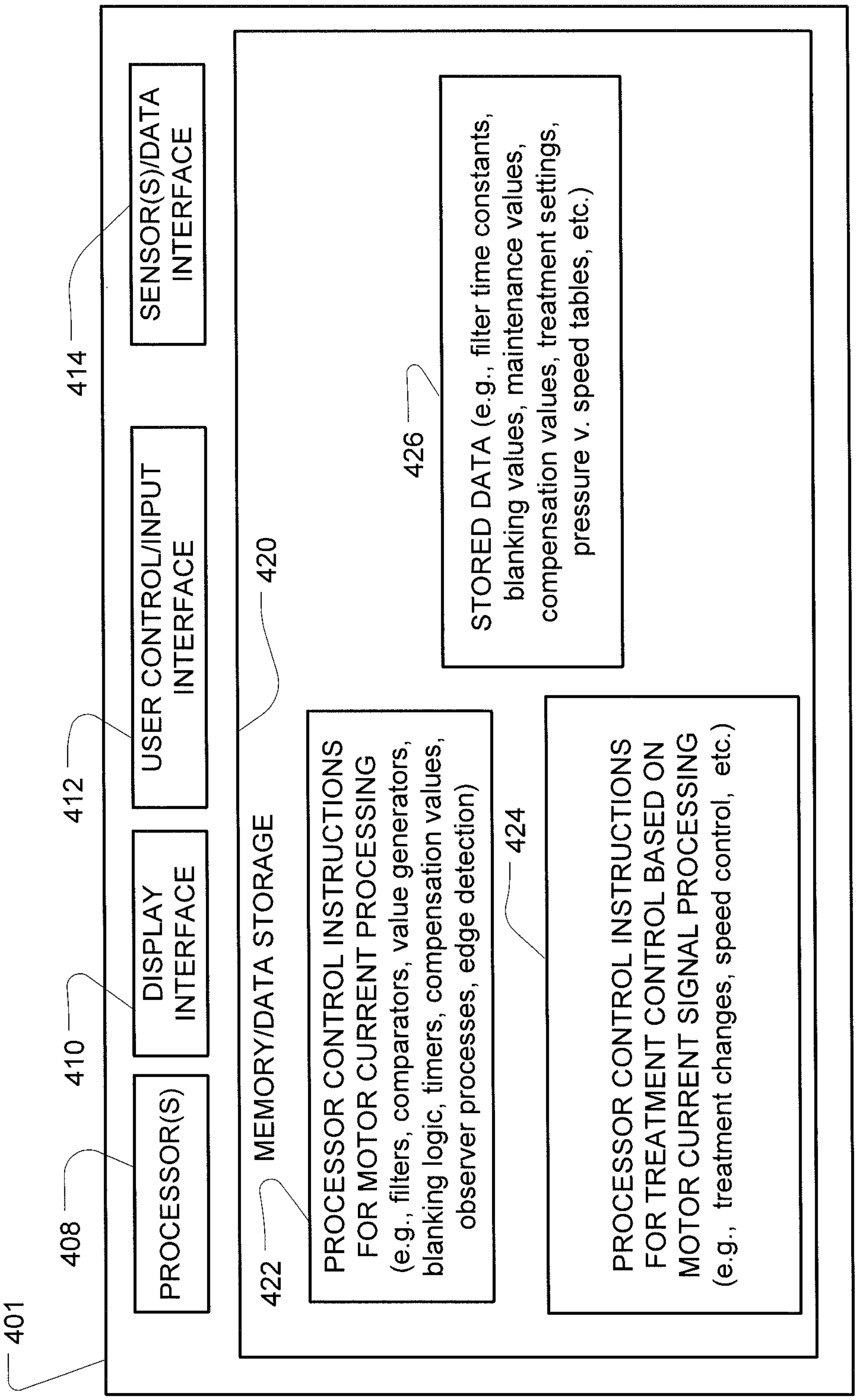
FIG. 4 is a block diagram illustrating example components of a system architecture for some embodiments of the present technology.

An example system architecture of such a controller suitable for the present technology is illustrated in the block diagram of FIG. 4. In the illustration, the controller 401 with the motor current analysis processes described herein for a respiratory treatment apparatus may include one or more processors 408. The system may also include a display interface 410 to output event detection reports (e.g., inspiration or expiration, etc.) as described herein such as on a monitor or LCD panel. A user control/input interface 412, for example, for a keyboard, touch panel, control buttons, mouse etc. may also be provided to activate or modify the control methodologies described herein. The system may also include a sensor or data interface 414, such as a bus, for receiving/transmitting data such as programming instructions, current signals, speed signals, back EMF signals, motor control signals etc. The device may also typically include memory/data storage components 420 containing control instructions of the aforementioned methodologies (e.g., FIGS. 2 and 3). These may include processor control instructions for motor current signal processing (e.g., preprocessing methods, filters, value generators, blanking or maintenance value generation logic, timers, compensation generation logic, observer processes, edge detectors, etc.) at 422. These may also include processor control instructions for treatment control based on motor current signal processing (e.g., treatment changes, speed control, etc.) at 424 as discussed in more detail herein. Finally, they may also include stored data 426 for these methodologies such filter time constants, filter parameters, blanking values, maintenance values, compensation values, treatment settings, pressure v. speed setting tables, etc.). In some embodiments, these processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

Example Respiratory Treatment Apparatus 1.1 Treatment Systems

Figure 5:
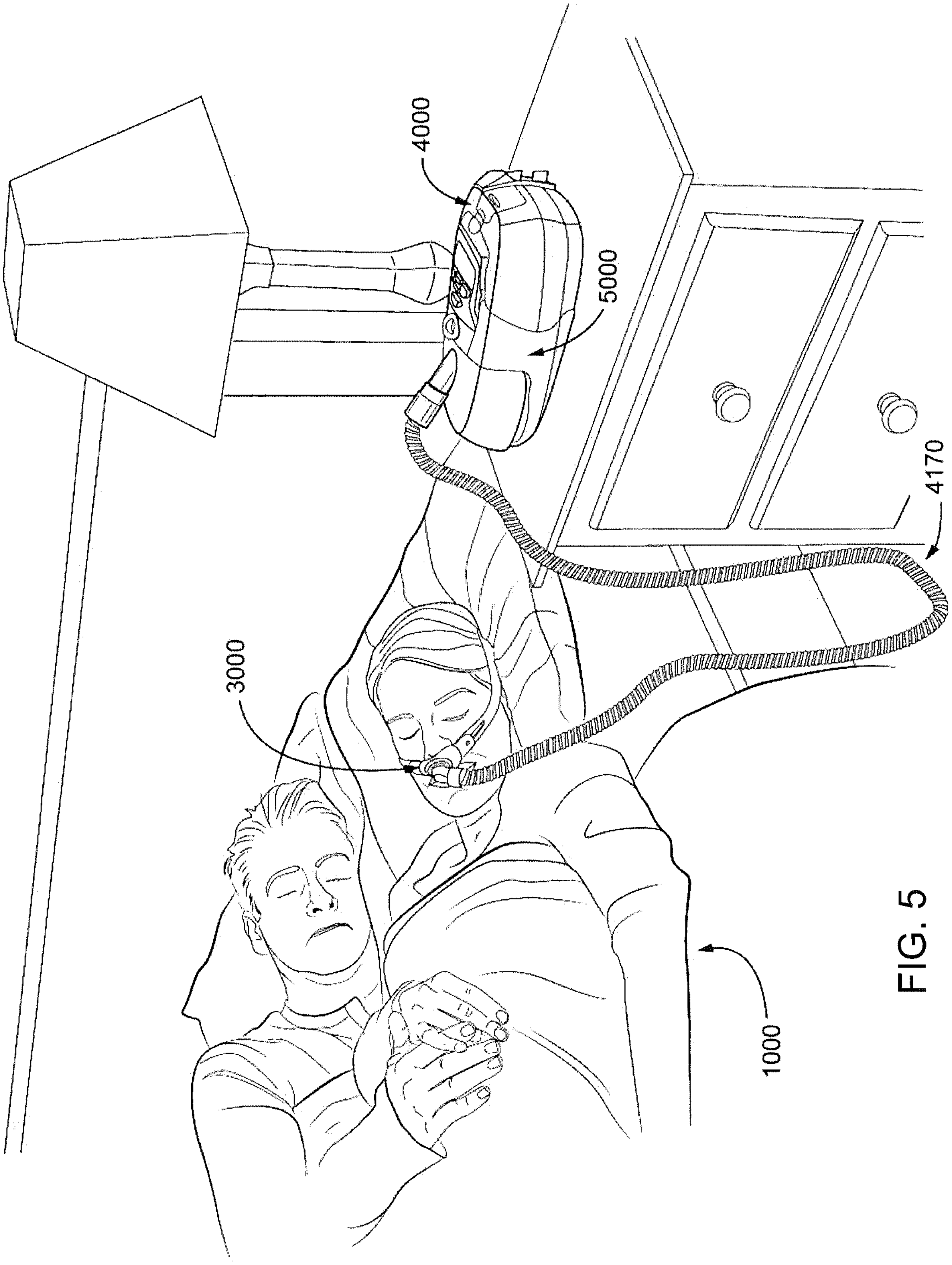
FIG. 5 shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.

In one form, the present technology may form part of an apparatus for treating a respiratory disorder, such as that illustrated in FIGS. 5 and 7*a*. The apparatus may include a flow generator or blower for supplying pressurised respiratory gas, such as air, to the patient 1000 via an air delivery tube leading to a patient interface 3000.

1.2 Therapy

In one form, the present technology may serve as part of a method for treating a respiratory disorder comprising the step of applying positive pressure to the entrance of the airways of a patient 1000, such as to the nasal passages of the patient via one or both nares and/or the mouth. For example, the PAP device 4000 may generate a Nasal Continuous Positive Airway Pressure (CPAP) therapy to treat Obstructive Sleep Apnea (OSA) of the upper airway by pushing the soft palate and tongue forward and away from the posterior oropharyngeal wall.

The PAP device 4000 may generate a Non-invasive ventilation (NIV) has been used to treat CSR, OHS, COPD, MD and Chest Wall disorders. In some cases of NIV, the pressure treatment may be controlled to enforce a target ventilation by measuring a tidal volume or minute ventilation, for example, and controlling the measure of ventilation to satisfy the target ventilation. Servo-controlling of the measure of ventilation, such as by a comparison of an instantaneous measure of ventilation and a long term measure of ventilation, may serve as a treatment to counteract CSR. In some such cases, the form of the pressure treatment delivered by an apparatus may be Pressure Support ventilation. Such a pressure treatment typically provides generation of a higher level of pressure during inspiration (e.g., an IPAP) and generation of a lower level of pressure during expiration (e.g., an EPAP).

1.3 Patient Interface 3000

Figure 6:
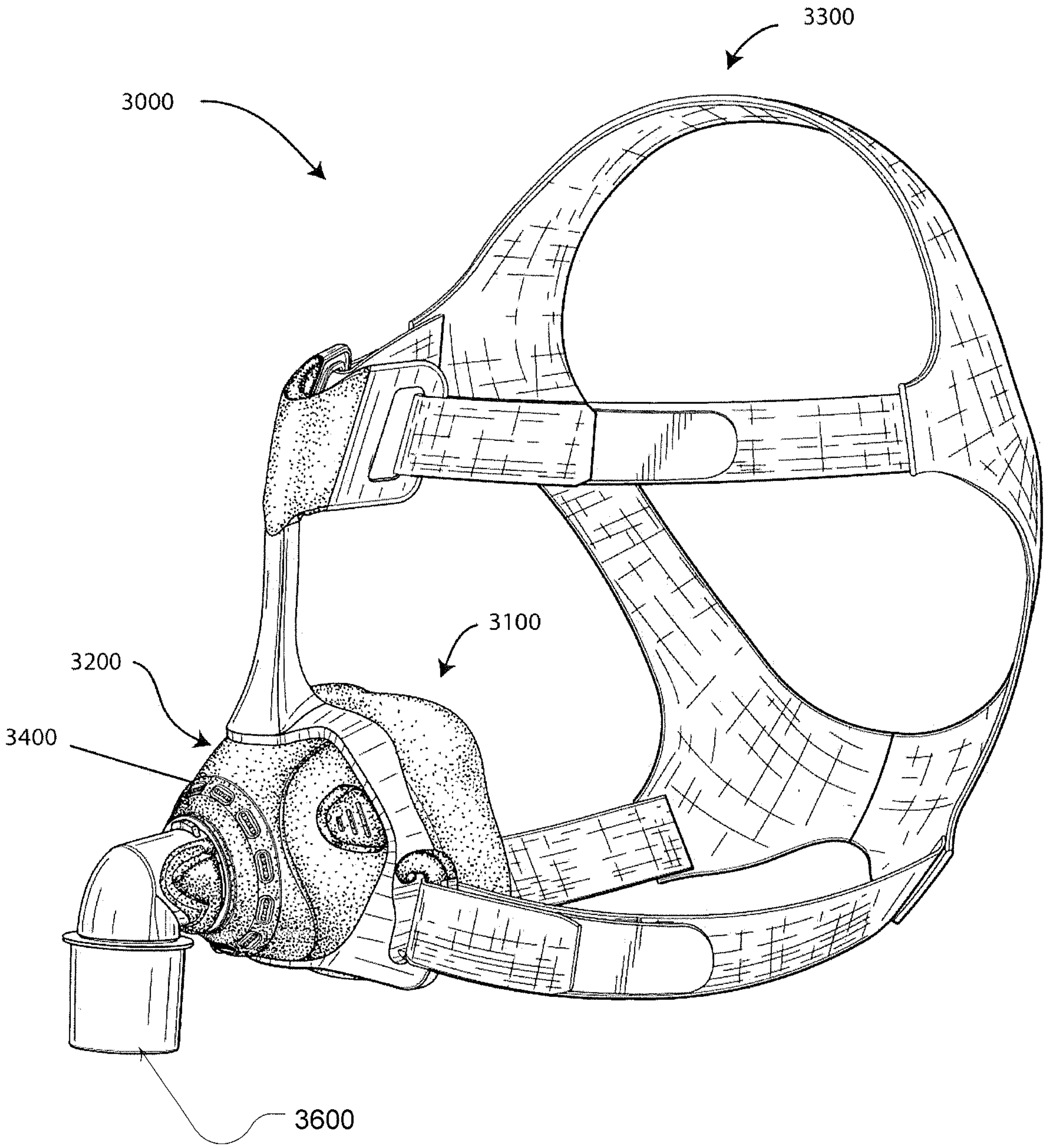
FIG. 6 shows a patient interface in accordance with one form of the present technology.

As illustrated in FIG. 6, a non-invasive patient interface 3000 in accordance with one aspect of the present technology may include the following functional aspects: a seal-forming structure 3100, a plenum chamber 3200, a positioning and stabilising structure 3300 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

1.4 PAP Device 4000

Figure 7B:
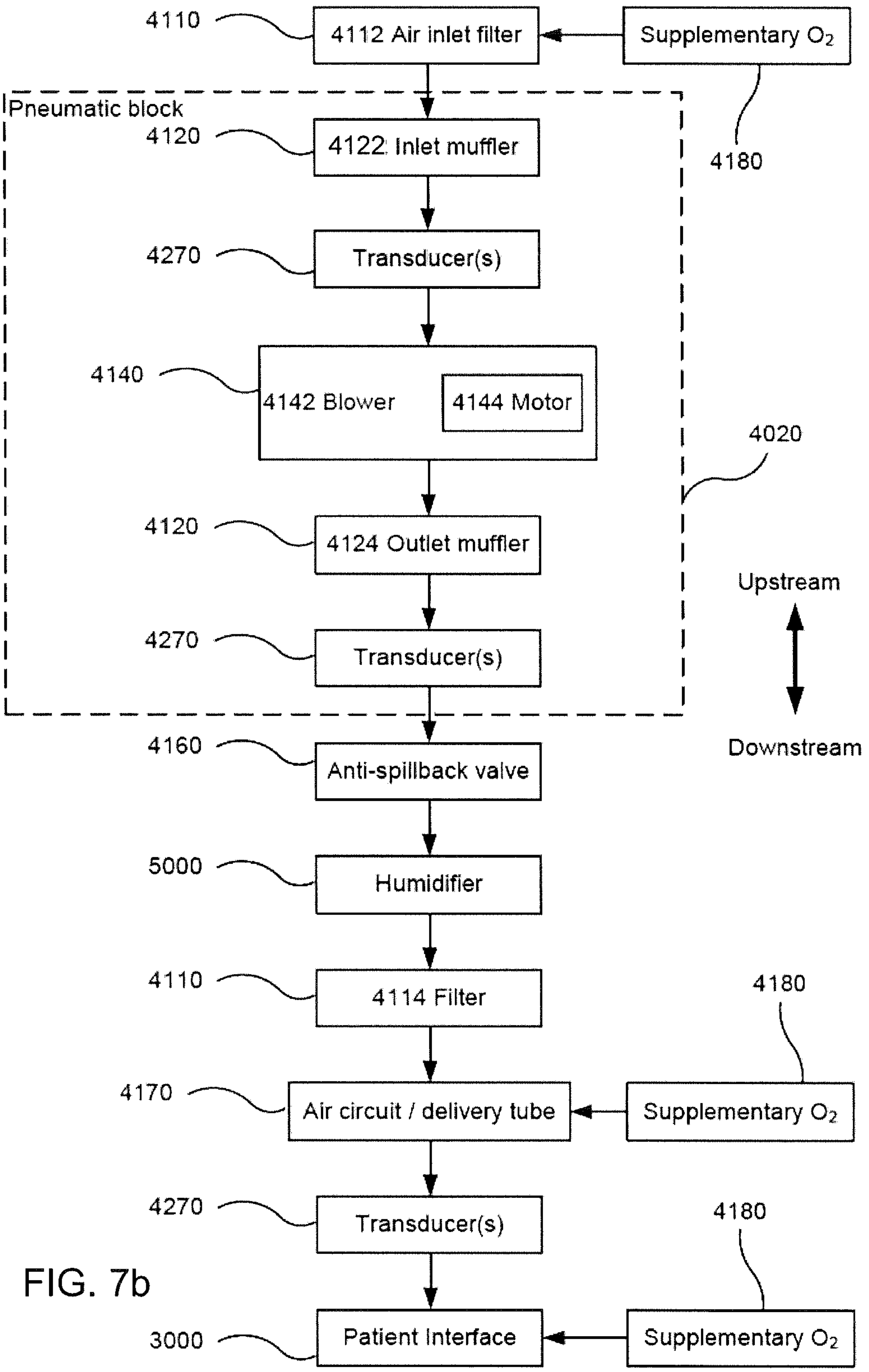
Figure 7C:
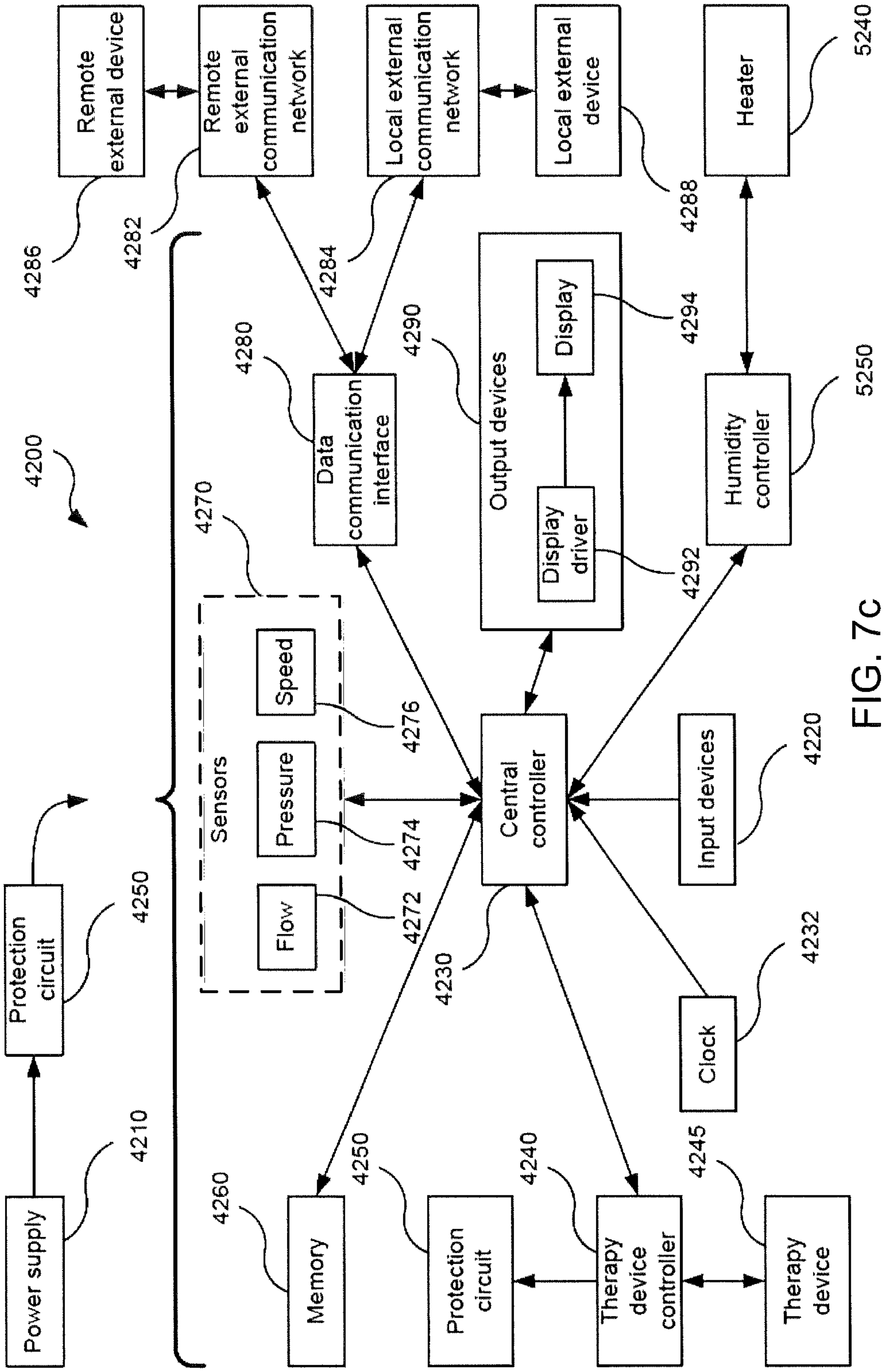

As illustrated in FIGS. 7*a*, 7*b* and 7*c*, an example PAP device 4000 in accordance with one aspect of the present technology may include mechanical and pneumatic components 4100, electrical components 4200 and may be programmed to execute one or more algorithms. The PAP device may have an external housing 4010 formed in two parts, an upper portion 4012 of the external housing 4010, and a lower portion 4014 of the external housing 4010. In alternative forms, the external housing 4010 may include one or more panel(s) 4015. The PAP device 4000 may include a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 may include an inlet air filter 4112, an inlet muffler 4122, a controllable pressure device 4140 capable of supplying air at positive pressure (preferably a blower 4142), and an outlet muffler 4124. One or more pressure sensors (e.g., pressure transducer 4272) and flow sensors (e.g., flow transducer 4274) may optionally be included in the pneumatic path.

The pneumatic block 4020 comprises a portion of the pneumatic path that is located within the external housing 4010.

The PAP device 4000 has an electrical power supply 4210, one or more input devices 4220, a central controller 4230, a therapy device controller 4240, a therapy device 4245, one or more protection circuits 4250, memory 4260, optional transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The central controller 4230 of the PAP device 4000 may be programmed to execute one or more algorithm modules, including in one implementation a pre-processing module, a therapy engine module, a pressure control module, and a fault condition module.

In what follows, the PAP device 4000 is referred to interchangeably as a ventilator.

1.4.1 PAP Device Mechanical & Pneumatic Components 4100

1.4.1.1 Air Filter(s) 4110

A PAP device in accordance with one form of the present technology may include an air filter 4110, or a plurality of air filters 4110.

In one form, an inlet air filter 4112 is located at the beginning of the pneumatic path upstream of a blower 4142. See FIG. 7*b*.

In one form, an outlet air filter 4114, for example an antibacterial filter, is located between an outlet of the pneumatic block 4020 and a patient interface 3000. See FIG. 7*b*.

1.4.1.2 Muffler(s) 4120

In one form of the present technology, an inlet muffler 4122 is located in the pneumatic path upstream of a blower 4142. See FIG. 7*b*.

In one form of the present technology, an outlet muffler 4124 is located in the pneumatic path between the blower 4142 and a patient interface 3000. Sec FIG. 7*b*.

1.4.1.3 Pressure device 4140

In one form of the present technology, a pressure device 4140 for producing a flow of air at positive pressure is a controllable blower 4142. For example, the blower may include a brushless DC motor 4144 with one or more impellers housed in a volute. The blower is capable of delivering a supply of air, for example about 120 litres/minute, at a positive pressure in a range from about 4 $cmH_2O$ to about 20 $cmH_2O$, or in other forms up to about 30 $cmH_2O$.

The pressure device 4140 is under the control of the therapy device controller 4240.

1.4.1.4 Transducer(s) 4270

In one form of the present technology, one or more transducers 4270 may be located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

1.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

1.4.1.6 Air Circuit 4170

An air circuit 4170 in accordance with an aspect of the present technology is constructed and arranged to allow a flow of air or breathable gasses between the pneumatic block 4020 and the patient interface 3000.

1.4.1.7 Oxygen Delivery

In one form of the present technology, supplemental oxygen 4180 may be delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

1.4.2 PAP Device Electrical Components 4200

1.4.2.1 Power Supply 4210

In one form of the present technology power supply 4210 is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

1.4.2.2 Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

1.4.2.3 Central Controller 4230

In one form of the present technology, the central controller 4230 is a processor suitable to control a PAP device 4000 such as an x86 INTEL processor.

A processor suitable to control a PAP device 4000 in accordance with another form of the present technology includes a processor based on ARM Cortex-M processor from ARM Holdings. For example, an STM32 series microcontroller from ST MICROELECTRONICS may be used.

Another processor suitable to control a PAP device 4000 in accordance with a further alternative form of the present technology includes a member selected from the family ARM9-based 32-bit RISC CPUs. For example, an STR9 series microcontroller from ST MICROELECTRONICS may be used. In certain alternative forms of the present technology, a 16-bit RISC CPU may be used as the processor for the PAP device 4000. For example a processor from the MSP430 family of microcontrollers, manufactured by TEXAS INSTRUMENTS, may be used.

The processor is configured to receive input signal(s) from one or more transducers 4270, and one or more input devices 4220.

The processor is configured to provide output signal(s) to one or more of an output device 4290, a therapy device controller 4240, a data communication interface 4280 and humidifier controller 5250.

The processor, or multiple such processors, may be configured to implement one or more methodologies described herein such as one or more algorithms expressed as computer programs stored in memory 4260. In some cases, as previously discussed, such processor(s) may be integrated with a PAP device 4000. However, in some devices the processor(s) may be implemented discretely from the flow generation components of the PAP device, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

1.4.2.4 Clock 4232

Preferably PAP device 4000 includes a clock 4232 that is connected to processor.

1.4.2.5 Therapy Device Controller 4240

In one form of the present technology, therapy device controller 4240 is a pressure control module that forms part of the algorithms executed by the processor.

In one form of the present technology, therapy device controller 4240 may include a dedicated motor control integrated circuit. For example, in one form a MC33035 brushless DC motor controller, manufactured by ONSEMI is used. In some embodiments, the therapy device controller 4240 may include one or more of the components of FIG. 2, which may be coupled with the bridge circuit of the motor of the therapy device 4245.

1.4.2.6 Protection Circuits 4250

Optionally a PAP device 4000 in accordance with the present technology includes one or more protection circuits 4250.

One form of protection circuit 4250 in accordance with the present technology is an electrical protection circuit.

One form of protection circuit 4250 in accordance with the present technology is a temperature or pressure safety circuit.

1.4.2.7 Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 includes removable form of memory 4260, for example a memory card made in accordance with the Secure Digital (SD) standard.

1.4.2.8 Transducers 4270

Optional transducers may be internal of the device, or external of the PAP device. External transducers may be located for example on or form part of the air delivery circuit, e.g. the patient interface. External transducers may be in the form of non-contact sensors such as a Doppler radar movement sensor that transmit or transfer data to the PAP device.

1.4.2.8.1 Flow 4274

An optional flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal or total flow Qt signal, from the flow transducer 4274, is received by the processor. However, other sensors for producing such a flow signal or estimating flow may be implemented. For example, a mass flow sensor, such as a hot wire mass flow sensor, may be implemented to generate a flow signal in some embodiments. Optionally, flow may be estimated from one or more signals of other sensors described here, such as in accordance with any of the methodologies described in a U.S. patent application Ser. No. 12/192,247, the disclosure of which is incorporated herein by reference.

Pressure

An optional pressure transducer 4272 in accordance with the present technology may be located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the processor. In one form, the signal from the pressure transducer 4272 is filtered prior to being received by the processor.

Motor Speed

In one form of the present technology motor speed signal 4276 may be generated. A motor speed signal 4276 may be provided by therapy device controller 4240. Motor speed may, for example, be generated by an optional speed sensor, such as a Hall effect sensor, or inferred from back EMF as previously described.

Data Communication Systems

In one form of the present technology, a data communication interface 4280 is provided, and is connected to processor. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor. In another form, data communication interface 4280 is an integrated circuit that is separate from processor.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

Output devices 4290 including optional display, alarms, etc.

An output device 4290 in accordance with the present technology may take the form of one or more of a visual, audio and haptic unit. A visual display may be a Liquid Crystal Display (LCD) or Light Emitting Diode (LED) display.

Display Driver 4292

A display driver 4292 receives as an input the characters, symbols, or images intended for display on the display 4294, and converts them to commands that cause the display 4294 to display those characters, symbols, or images.

Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

Therapy Device 4245

In a preferred form of the present technology, the therapy device 4245 is under the control of a controller to deliver therapy to a patient 1000.

Preferably the therapy device 4245 is a positive air pressure device 4140.

Humidifier 5000

In one form of the present technology there is provided a humidifier 5000, such as the example illustrated in FIG. 8. The humidifier may include a water reservoir and a heating plate 5240 as shown in FIG. 7*c*.

Although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

Additional Technology Examples

Example 1. A method of a respiratory treatment apparatus for determining an indication of inspiration or expiration, the method comprising:

- measuring current supplied to a blower configured to provide a respiratory treatment;
- deriving first and second current signals from the measured current, the first derived current signal being a long term measure of current, the second derived current signal being a short term measure of current; and
- determining with a processor an indication of inspiration or expiration as a function of the first derived current signal and the second derived current signal.

Example 2. The method of Example 1 wherein the first derived current signal is derived by filtering of the measured current.

Example 3. The method of Example 2 wherein the first derived current signal is derived by a low pass filter with a first time constant.

Example 4. The method of any one of Examples 1 to 3 wherein the second derived current signal is derived by filtering of the measured current.

Example 5. The method of Example 3 wherein the second derived current signal is derived by a low pass filter with a second time constant.

Example 6. The method of Example 3 wherein the first time constant is on the order of a time period shorter than an average breath and the second time constant is on the order of a time period greater than an average breath.

Example 7. The method of any one of the preceding Examples wherein the function of the first derived current signal and the second derived current signal comprises a comparison of the first derived current signal and the second derived current signal.

Example 8. The method of any one of the preceding Examples further comprising adding a compensation signal to the first derived current signal.

Example 9. The method of any one of the preceding Examples further comprising adding a compensation signal to the first derived current signal based on the indication of inspiration or expiration.

Example 10. The method of any one of the preceding Examples wherein different compensation signals are added to the first derived current signal based on the indication of inspiration or expiration.

Example 11. The method of any one of Examples 8 to 10 wherein the function of the first derived current signal and the second derived current signal comprises a comparison of the second derived current signal and the sum of the first derived current signal and a compensation signal.

Example 12. The method of any one of the preceding Examples further comprising maintaining the second derived current signal with blanking values rather than the measure of current during a transition of the indicator of inspiration or expiration.

Example 13. The method of any one of the preceding Examples further comprising, controlling with the processor setting of a pressure treatment generated by the blower based on the indication of inspiration or expiration.

Example 14. A respiratory treatment apparatus for determining an indication of inspiration or expiration, the apparatus comprising:

- a blower, including an impeller and motor, the blower configured to generate a pressure treatment to a patient interface;
- a current sensing circuit configured to generate a
- current signal representative of current supplied to the motor; and
- a processor coupled to the sensing circuit, the processor configured to: (a) derive first and second current signals from the current sensing circuit, the first derived current signal being a long term measure of current, the second derived current signal being a short term measure of current, and (b) determine an indication of inspiration or expiration as a function of the first derived current signal and the second derived current signal.

Example 15. The apparatus of Example 14 wherein the processor comprises a filter to generate the first derived current signal by filtering of the measured current.

Example 16. The apparatus of Example 15 wherein the filter comprises a low pass filter with a first time constant.

Example 17. The apparatus of any one of Examples 14 to 16 further comprising a further filter to generate the second derived current signal by filtering of the first derived current signal.

Example 18. The apparatus of Example 16 wherein the processor further comprises a further filter to generate the first derived current signal by filtering of the second derived current signal, the further filter comprising a low pass filter with a second time constant, wherein the first time constant is on the order of a time period shorter than an average breath and the second time constant is on the order of a time period greater than an average breath.

Example 19. The apparatus of any one of Examples 14 to 18 wherein the function of the first derived current signal and the second derived current signal comprises a comparison of the first derived current signal and the second derived current signal.

Example 20. The apparatus of any one of Examples 14 to 18 wherein the processor is further configured to add a compensation signal to the first derived current signal.

Example 21. The apparatus of any one of Examples 14 to 18 wherein the processor is further configured to add a compensation signal to the first derived current signal as a function of the determined indication of inspiration or expiration.

Example 22. The apparatus of any one of Examples 20 and 21 wherein the processor is configured to add different compensation signals to the first derived current signal based on the determined indication of inspiration or expiration.

Example 23. The apparatus of any one of Examples 14 to 19 and 21 to 22 wherein the function of the first derived current signal and the second derived current signal comprises a comparison of the second derived current signal and the sum of the first derived current signal and a compensation signal.

Example 24. The apparatus of any one of Examples 14 to 23 wherein the processor is further configured to maintain the first derived current signal with blanking values rather than the measure of current during a transition associated with the determined indicator of inspiration or expiration.

Example 25. The apparatus of any one of Examples 14 to 24 wherein the processor is further configured to control setting of a pressure treatment generated by the blower based on the indication of inspiration or expiration.

The invention claimed is:

1. A method of a blower speed controller of a respiratory treatment apparatus, the method comprising:

- repeatedly measuring current supplied to a blower configured to provide a respiratory treatment;
- repeatedly deriving first and second current signals from the measured current by filtering the measured current, the first derived current signal being a long term measure of current, the second derived current signal being a short term measure of current;
- in a first state, generating a command signal to set motor speed of the blower for an expiration pressure;
- in a second state, generating a command signal to run motor speed of the blower for the expiration pressure;
- in a third state, generating a command signal to set a motor speed of the blower for an inspiration pressure;
- in a fourth state, generating a command signal to run motor speed of the blower for the inspiration pressure; and
- based on comparing of the first derived current signal and the second derived current signal, transitioning between states comprising one or both of: transitioning between the second state and the third state, and transitioning between the fourth state and the first state.

2. The method of claim 1, further comprising, based on an assessment of a measure of time or a measure of speed, further transitioning between states comprising one or both of transitioning between the first state and the second state and transitioning between the third state and the fourth state.

3. The method of claim 2, wherein transitioning between the first state and the second state comprises transitioning to an intermediary state from the first state and transitioning from the intermediary state to the second state, wherein transitioning from the intermediary state to the second state is based on a predetermined delay.

4. The method of claim 2, wherein transitioning between the third state and the fourth state comprises transitioning to an intermediary state from the third state and transitioning from the intermediary state to the fourth state, wherein transitioning from the intermediary state to the fourth state is based on a predetermined delay.

5. The method of claim 1, further comprising compensating, with values of current, the first derived current signal based on an indication of inspiration, and compensating, with values of current, the first derived current signal based on an indication of expiration.

6. The method of claim 1, wherein the first derived current signal is derived by a low pass filter with a first time constant.

7. The method of claim 6, wherein the second derived current signal is derived by a low pass filter with a second time constant.

8. The method of claim 7, wherein the first time constant is on an order of a time period greater than an average breath, and the second time constant is on an order of a time period shorter than an average breath.

9. The method of claim 1, wherein the comparing of the first derived current signal and the second derived current signal is performed by a comparator.

10. The method of claim 9, wherein a negative compensation signal is added to the first derived current signal based on an indication of inspiration, and a positive compensation signal is added to the first derived current signal based on an indication of expiration.

11. The method of claim 1, further comprising maintaining the first derived current signal with blanking values rather than the measure of current during a transition in blower motor speed between an inspiratory speed and an expiratory speed.

12. The method of claim 1, further comprising compensating with values of current by determining a value of current that is proportional to a peak value of current of the first derived current signal.

13. A respiratory treatment apparatus for determining an indication of inspiration or expiration, the apparatus comprising:

- a blower, including an impeller and motor, the blower configured to generate a respiratory treatment for a patient interface;
- a current sensing circuit configured to generate a current signal representative of current supplied to the motor; and
- a controller coupled to the current sensing circuit, the controller configured to: (a) derive first and second current signals by filtering the current signal from the current sensing circuit, the first derived current signal being a long term measure of current, the second derived current signal being a short term measure of current, and (b) repeatedly determine indications of inspiration or expiration by comparison of the first derived current signal and the second derived current signal,
- wherein the controller is configured to:
  - in a first state, generate a command signal to set motor speed of the blower for an expiration pressure;
  - in a second state, generate a command signal to run motor speed of the blower for the expiration pressure;
  - in a third state, generate a command signal to set a motor speed of the blower for an inspiration pressure;
  - in a fourth state, generate a command signal to run motor speed of the blower for the inspiration pressure; and
  - based on comparing of the first derived current signal and the second derived current signal, transition between states comprising one or both of: transitioning between the second state and the third state, and transitioning between the fourth state and the first state.

14. The respiratory treatment apparatus of claim 13, wherein the controller is further configured to, based on an assessment of a measure of time or a measure of speed, further transition between states comprising one or both of: transitioning between the first state and the second state, and transitioning between the third state and the fourth state.

15. The respiratory treatment apparatus of claim 14, wherein a transition between the first state and the second state comprises a transition to an intermediary state from the first state and a transition from the intermediary state to the second state, wherein a transition from the intermediary state to the second state is based on a predetermined delay.

16. The respiratory treatment apparatus of claim 14, wherein a transition between the third state and the fourth state comprises a transition to an intermediary state from the third state and a transition from the intermediary state to the fourth state, wherein a transition from the intermediary state to the fourth state is based on a predetermined delay.

17. The respiratory treatment apparatus of claim 13, wherein the controller is further configured to compensate, with values of current, the first derived current signal based on an indication of inspiration, and compensate, with values of current, the first derived current signal based on an indication of expiration.

18. The respiratory treatment apparatus of claim 13, wherein the controller comprises a filter to generate the second derived current signal by filtering of the current signal.

19. The respiratory treatment apparatus of claim 18, wherein the filter comprises a low pass filter with a first time constant.

20. The respiratory treatment apparatus of claim 18, the controller comprises a further filter to generate the first derived current signal by filtering of the second derived current signal or the current signal.

21. The respiratory treatment apparatus of claim 19 wherein the controller further comprises a further filter to generate the first derived current signal by filtering of the second derived current signal, the further filter comprising a low pass filter with a second time constant, wherein the first time constant is on an order of a time period shorter than an average breath, and the second time constant is on an order of a time period greater than an average breath.

22. The respiratory treatment apparatus of claim 17, wherein the controller is configured to add a negative compensation signal to the first derived current signal based on a determined indication of inspiration, and to add a positive compensation signal to the first derived current signal based on a determined indication of expiration.

23. The respiratory treatment apparatus of claim 13, wherein the controller is configured to maintain the first derived current signal with blanking values rather than a measure of the supplied current during a transition in blower motor speed between an inspiratory speed and an expiratory speed.

* * * * *